United States Patent [19]
Miyagi

[11] Patent Number: 5,683,413
[45] Date of Patent: Nov. 4, 1997

[54] FORCEPS INSTRUMENT FOR ENDOSCOPE

[75] Inventor: Kunihiko Miyagi, Tokyo, Japan

[73] Assignee: Machida Endoscope Co., Ltd., Tokyo, Japan

[21] Appl. No.: 682,952

[22] Filed: Jul. 18, 1996

[30] Foreign Application Priority Data

Aug. 3, 1995 [JP] Japan .................. 7-218094

[51] Int. Cl.⁶ .................................................. A61B 17/28
[52] U.S. Cl. .................. 606/205; 606/170; 606/208
[58] Field of Search .................. 606/205, 206, 606/208, 167, 170, 174

[56] References Cited

U.S. PATENT DOCUMENTS

| | | |
|---|---|---|
| 4,889,106 | 12/1989 | Watanabe . |
| 5,293,878 | 3/1994 | Bales et al. ............................ 606/170 |
| 5,591,202 | 1/1997 | Slater et al. ............................ 606/170 |

*Primary Examiner*—Michael Buiz
*Assistant Examiner*—Kevin Truong
*Attorney, Agent, or Firm*—Fish & Richardson P.C.

[57] ABSTRACT

A pair of forceps cups disposed on a distal end of an elongated guide tube is opened and closed by remote control of a control mechanism disposed on a rear end of the guide tube through a wire within the guide tube. The control mechanism includes a holder having a rod portion, and a slider slidably disposed on the rod portion. A receiving member is mounted on a rear end portion of the wire at a forward position of the slider. This receiving member is biased backwardly by a compressed coil spring. The slider is not connected to the rear end portion of the wire. During the course of a forward movement of the slider, the slider contacts the receiving member and causes the wire to move forwardly through this receiving member. As a consequence, the pair of forceps cups is opened. When the slider is moved backwardly, the wire is pulled under the effect of the coil spring. Consequently, the pair of forceps cups is closed.

8 Claims, 4 Drawing Sheets

FORCEPS INSTRUMENT FOR ENDOSCOPE

BACKGROUND OF THE INVENTION

This invention relates to a forceps instrument for an endoscope.

In general, an endoscope employs a forceps instrument of the type as disclosed in FIGS. 4 through 6 of U.S. Pat. No. 4,889,106. This forceps has an elongated guide tube to be pierced into a channel of the endoscope. A pair of openable and closable forceps cups is mounted on a distal end of the guide tube. A control mechanism is disposed on a rear end of the guide tube. A wire for associating the forceps cups with the control mechanism is inserted into the guide tube. The pair of forceps cups is connected to a distal end of the wire through a link mechanism. The control mechanism comprises a holder having an elongated rod portion, and a slider disposed on the rod portion of the holder for sliding forwardly and backwardly. The rod portion of the holder is connected to the rear end of the guide tube, and the slider is connected to a rear end of the wire.

When the slider slides forwardly, the wire moves forwardly. The forwardly moving force of the wire is transmitted to the pair of forceps cups through the link mechanism. As a consequence, the pair of forceps cups is opened. When the slider slides backwardly, the wire is tensioned. This tensile force of the wire is transmitted to the pair of forceps cups through the link mechanism. As a consequence, the pair of forceps cups is closed. At that time, a piece of meat of an inner wall of a body cavity is torn off by the pair of forceps cups and received in the forceps cups.

Recently, as the endoscope was made smaller in diameter, the guide tube and the wire of the forceps instrument were also made smaller in diameter. For this reason, when the pair of forceps cups is closed, if the wire is tensioned with the same force as heretofore applied, there is a possibility to cut off the wire.

SUMMARY OF THE INVENTION

It is an object of the present invention to provide a forceps instrument in which the possibility of occurrence of wire-cut may be minimized.

According to the present invention, there is provided a forceps instrument for an endoscope comprising:

(a) a guide tube capable of piercing all the way through a channel of the endoscope;

(b) a wire extending through the guide tube;

(c) a pair of forceps cups openably and closably provided on a distal end of the guide tube;

(d) a link mechanism for connecting a distal end of the wire with the pair of forceps cups, the link mechanism opening the pair of forceps cups in response to a forward movement of the wire and closing the pair of forceps cups in response to a backward movement of the wire; and (e) a control mechanism disposed on a rear end of the guide tube and for remote controlling the pair of forceps cups through the wire, the control mechanism comprising:

(i) a holder, the holder including a rod portion connected to the rear end of the guide tube, the rod portion having a receiving space;

(ii) a slider axially slidably disposed on the rod portion of the holder, the slider being disconnected from the wire;

(iii) receiving means mounted on a rear end portion of the wire in the receiving space of the holder, the receiving means being disposed forwardly of the slider and pushed by the slider when the slider slides forwardly; and (iv) a spring for biasing the receiving means backwardly.

DETAILED DESCRIPTION OF THE EMBODIMENT

Figure 1:
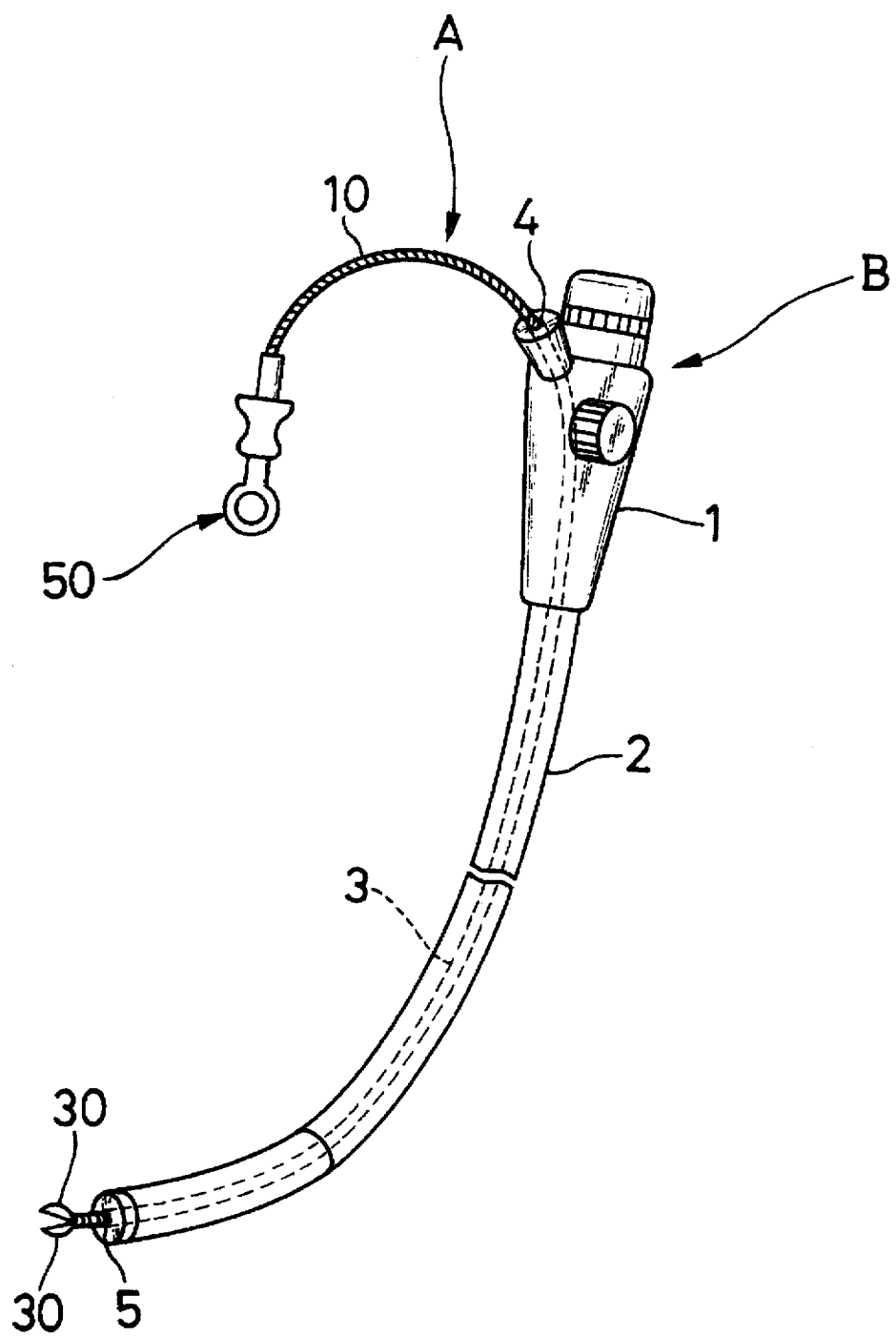
FIG. 1 is a perspective view showing one embodiment of a forceps instrument according to the present invention, together with an endoscope.

One embodiment of the present invention will now be described with reference to the accompanying drawings. As shown in FIG. 1, a forceps instrument A is used for an endoscope B.

The endoscope B is known and therefore, briefly described. As shown in FIG. 1, the endoscope 1 comprises a control body 1, and a flexible insertion portion 2 extending from the control body 1. A flexible tube is received in the control body 1 and insertion portion 2. A channel 3 is defined by this tube. An inlet port 4 of this channel 3 is opened at the control body 1, whereas an outlet port 5 is opened at a distal end face of the insertion portion 2.

Figure 2:
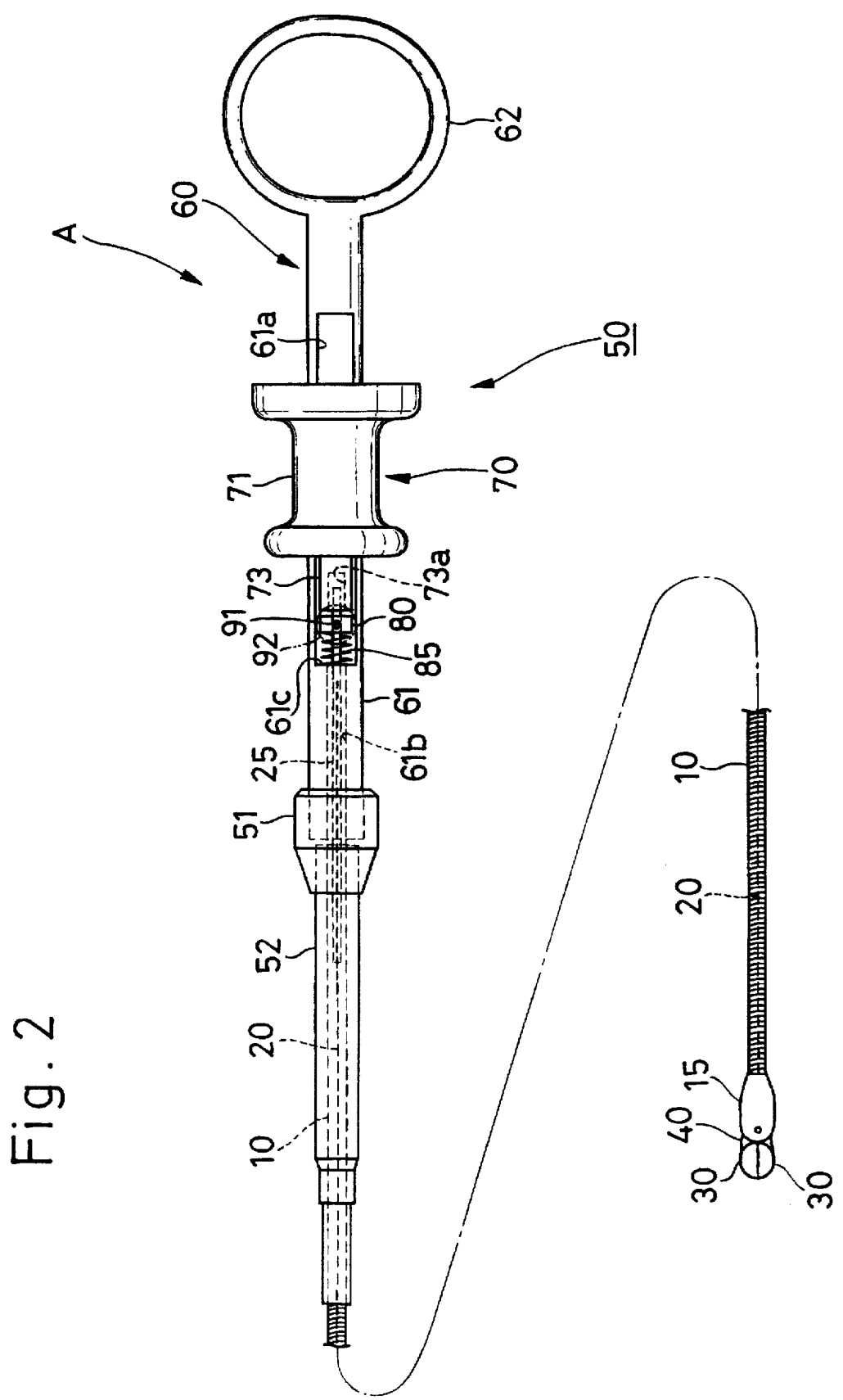
FIG. 2 is a side view showing an overall construction of the forceps instrument in which a handle portion of a fixing thread is omitted.

As shown in FIGS. 1 and 2, the forceps instrument A comprises an elongated guide tube 10 to be pierced into the channel 3 of the endoscope B, a wire 20 extending through this guide tube 10, a pair of openable and closable forceps cups 30 disposed on a distal end of the guide tube 10, and a control mechanism 50 disposed on a rear end of the guide tube 10 and for remote controlling the pair of forceps cups 30 through the wire 20.

Figure 3:
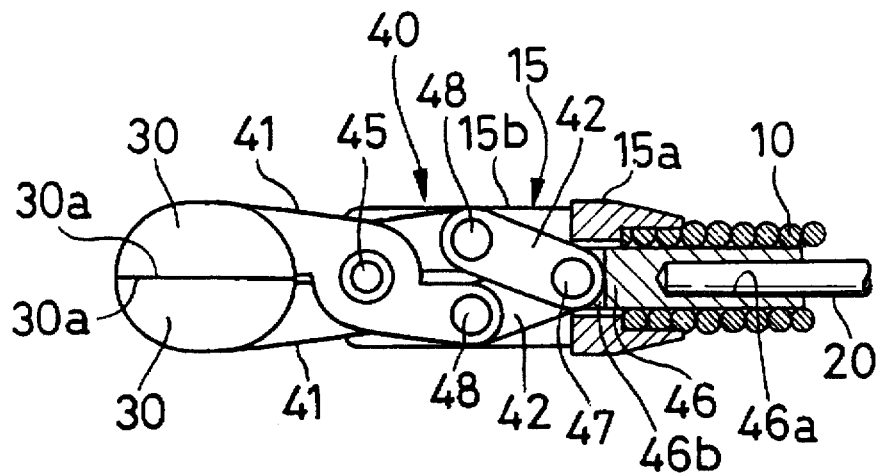
FIG. 3 is an enlarged side sectional view of a distal end portion of the forceps instrument, in which a pair of forceps cups is closed.
Figure 4:
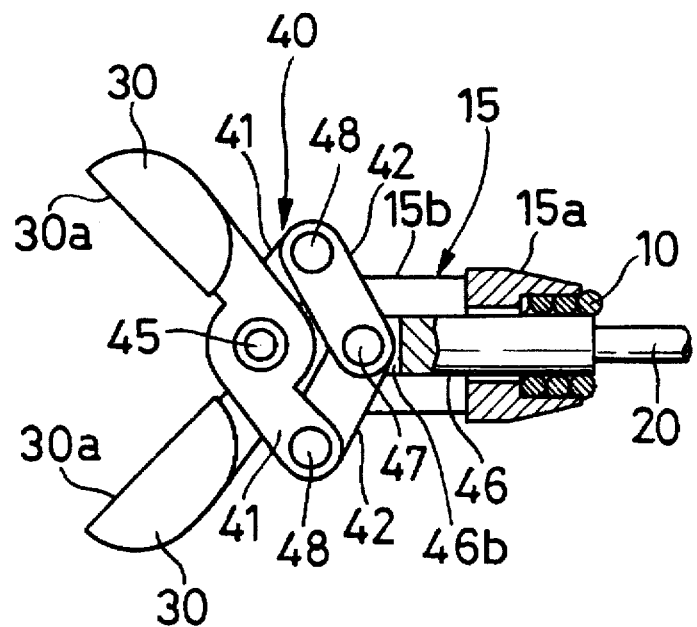
FIG. 4 is an enlarged side sectional view of the distal end portion of the forceps instrument, in which the pair of forceps cups is opened.

As shown in FIGS. 2 through 4, the guide tube 10 is constituted by a fine metal wire wound spirally and has flexible properties.

As shown in FIGS. 3 and 4, the pair of forceps cups 30 is connected to the distal end of the guide tube 10 through a support 15. This support 15 includes a sleeve-like basal portion 15a, and a pair of plate-like projections 15b (only one is shown) extending forwardly from the basal portion 15a. The distal end of the guide tube 10 is inserted into the basal portion 15a and fixed thereto by welding or the like. Intermediate portions of a pair of first arms 41 are pivotally mounted on distal end portions of the pair of projections 15b of the support 15 by a pin 45. The intermediate portions of the first arms 41 are disposed between the distal end portions of the projections 15b in an overlapping manner. The forceps cups 30 are mounted on distal end portions of the first arms 41, respectively.

A peripheral edge of each forceps cup 30 forms a cutting edge 30a. Those cutting edges 30a are in an opposing relation.

On the other hand, a cylindrical connecting rod 46 is connected to a distal end of the wire 20. Specifically, a hole 46a is formed in a rear end portion of the connecting rod 46. The hole 46 extends axially and opens at a rear end face of the connecting rod 46. The distal end of the wire 20 is inserted into the hole 46a and fixed by welding or the like. The connecting rod 46 is pierced into the basal portion 15a of the support 15 and further into the distal end portion of the guide tube 10. The connecting rod 46 is axially slidable.

The connecting rod 46 is provided at the distal end with a pair of projections 46b (only one is shown). Rear ends of a pair of second arms 42 are pivotally connected to the projections 46b by a pin 47. Distal ends of the second arms 42 are pivotally connected respectively to rear ends of the first arms 41 by a pin 48.

The connecting rod 46, the pins 45, 47, 48, the pair of first arms 41, and the pair of second arms 42 constitute a link mechanism 40 (pantagraph mechanism).

When the wire 20 moves forwardly, as shown in FIG. 4, the link mechanism 40 is contracted in an axial direction of the wire 20. As a consequence, the pair of forceps cups 30 is opened. When the wire 20 moves backwardly, as shown in FIG. 3, the link mechanism 40 is expanded in the axial direction of the wire 20. As a consequence, the pair of forceps cups 30 is closed.

A construction of the control mechanism 50 will now be described in detail with reference to FIGS. 2, 5 and 6. As best shown in FIG. 2, the control mechanism 50 comprises a holder 60, and a slider 70. The holder 60 includes an elongated rod portion 61, and a ring portion 62 formed on a rear end of the rod portion 61. A distal end of this rod portion 61 is connected to the rear end of the guide tube 10. That is, the rear end of the guide tube 10 is fixedly inserted into a sleeve 52. A rear end of the sleeve 52 and the distal end of the rod portion 61 of the holder 60 are connected to each other through a connector 51.

Figure 5:
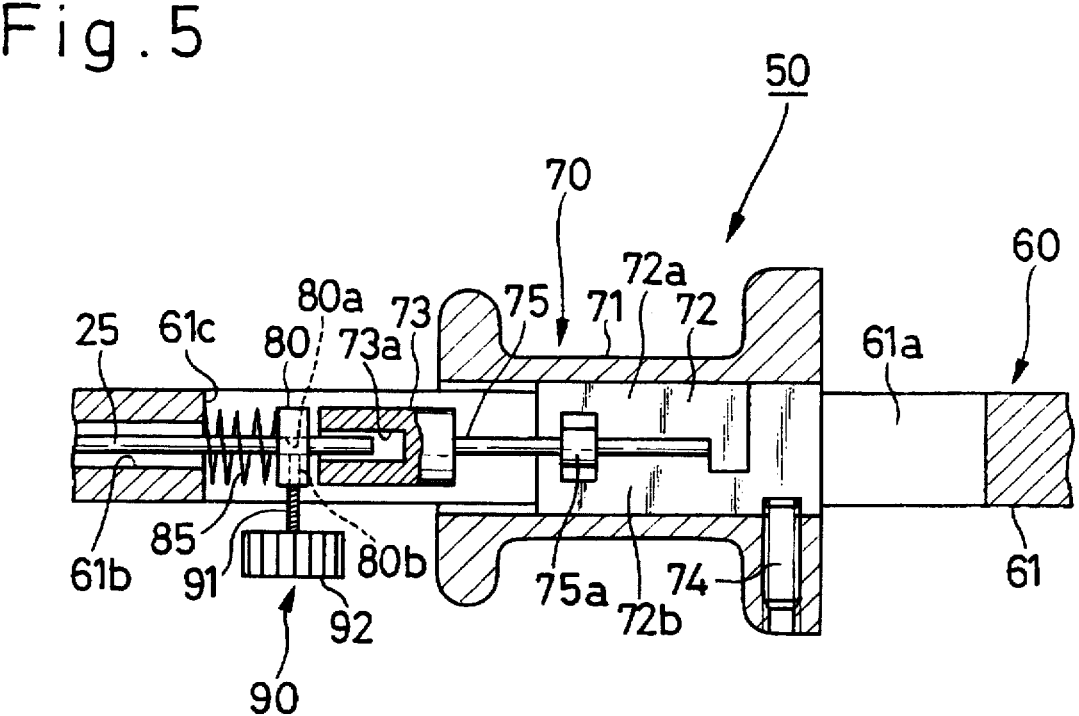
FIG. 5 is an enlarged plan sectional view showing a control mechanism of the forceps instrument.
Figure 6:
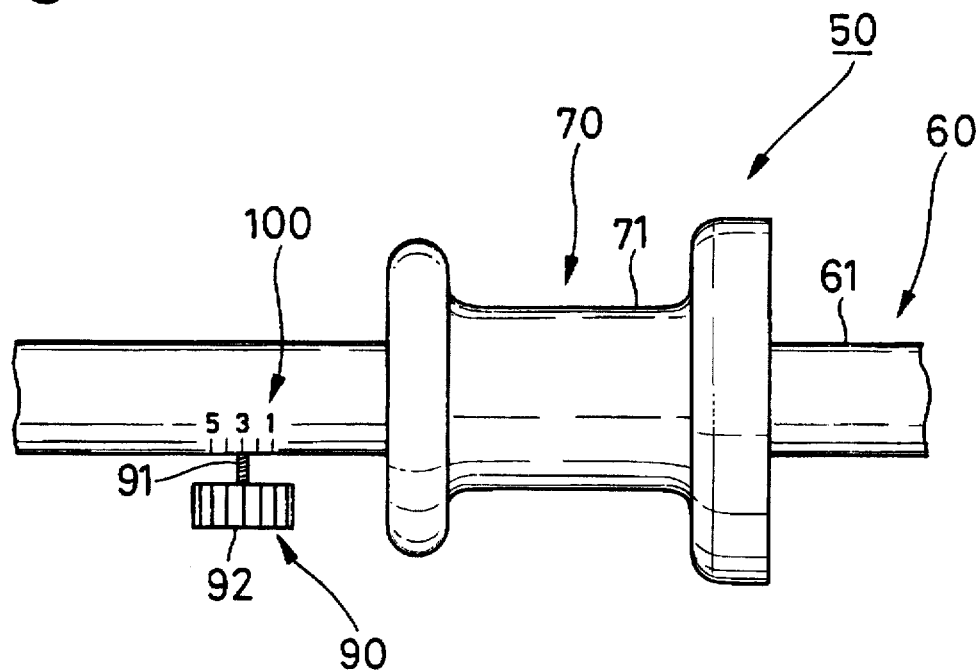
FIG. 6 is an enlarged plan view of the control mechanism.

As shown in FIGS. 2 and 5, a slit 61a (receiving space) is formed in an intermediate portion of the rod portion 61 of the holder 60. This slit 61a extends axially and opens at a peripheral surface of the rod portion 61. Another hole 61b is formed in a distal portion of the rod portion 61. The hole 61b is in communication with the slit 61a and extends axially. At a boundary between the slit 61a and the hole 61b, a step 61c (a surface defining a distal end of the slit 61a) is formed.

As best shown in FIG. 5, the slider 70 includes a slider body 71 disposed on an outer periphery of the rod portion 61 of the holder 60 and slidable in the axial direction of the rod portion 61, a connecting member 72, and a push member 73. The connecting member 72 and the push member 73 are slidably received within the slit 61a of the rod portion 61. The push member 73 is of a cylindrical configuration and has a receiving hole 73a. The receiving hole 73a extends axially and opens at a distal end face of the push member 73. A rod 75 extends axially of the rod portion 61 from a rear end of the push member 73. This rod 75 is connected to the connecting member 72. That is, the connecting member 72 is formed by welding two plates 72a, 72b. An enlarged diameter portion 75a of the rod 75 is sandwiched between the plates 72a and 72b, and thereby the rod 75 is connected to the connecting member 72. The connecting member 72 is connected to the slider body 71 through a fixing thread 74.

On the other hand, as shown in FIGS. 2 and 5, the rear end portion of the wire 20 is fixedly inserted into a terminal tube 25. This terminal tube 25 constitutes a part of the wire 20. The terminal tube 25 extends through the rear end portion of the guide tube 10, the connector 51 and the hole 61b of the rod portion 61, and projects into the slit 61a.

The rear end of the terminal tube 25 is not connected to the push member 73. The rear end of the terminal tube 25 is merely axially slidably inserted into the receiving hole 73a of the push member 73. The difference between the diameter of the receiving hole 73a and that of the terminal tube 25 is shown in an exaggerated manner in FIG. 5. The terminal tube 25 does not contact a bottom surface of the receiving hole 73a.

Within the slit 61a of the rod portion 61, a disk-like receiving member 80 (receiving means) is mounted on an outer periphery of a rear end portion of the terminal tube 25. The receiving member 80 is disposed forwardly of the push member 73. A compressed coil spring 85 is interposed between the receiving member 80 and the step 61c formed on the rod portion 61. The compressed coil spring 85 surrounds the terminal tube 25. The wire 20 is biased in a retracting direction by this coil spring 85.

A through-hole 80a is formed in the receiving member 80, and the rear end portion of the terminal tube 25 is pierced into this through-hole 80a. Accordingly, the location of the receiving member 80 can be adjusted along the terminal tube 25. A threaded hole 80b is radially formed in a peripheral wall of the receiving member 80 all the way therethrough. A threaded portion 91 (protrusion) of the fixing thread 90 (fixing means) is threadingly engaged with the threaded hole 80b. An inner end of the threaded portion 91 pushes the outer peripheral surface of the terminal tube 25 and thereby the receiving member 80 is fixed to the terminal tube 25. The threaded portion 91 extends in a direction perpendicular to the rod portion 61 from the slit 61a. A handle portion 92 is fixed to the outer end of the threaded portion 91.

Gradations 100 for confirming the location of the fixing thread 90, namely, the location of the receiving member 80, are formed on a peripheral surface of the rod portion 61 of the holder 60.

Operation of the forceps instrument A will now be described. In the state that the insertion portion 2 of the endoscope B is inserted in the patient's body cavity, the guide tube 10 of the forceps instrument A is pierced into the channel 3 of the endoscope B to cause the pair of forceps cups 30 disposed on the distal end of guide tube 10 to project from the distal end face of the insertion portion 2. In that state, the operator inserts the thumb of one hand into the ring portion 62 of the holder 60 and sandwiches the slider body 71 with the index finger and the middle finger in order to move the slider body 71 forwardly along the rod portion 61 of the holder 60. Then, during the course of this forward movement of the slider body 71, the distal end of the push member 73 fixed to the slider body 71 contacts the receiving member 80 to move the receiving member 80 forwardly against the effect of the coil spring 85. The forwardly moving force of the receiving member 80 is transmitted to the link mechanism 40 through the wire 20. As a consequence, the pair of forceps cups 30 is opened.

In the state the pair of forceps cups 30 is opened as mentioned, the operator causes the holder 60 to move forwardly to move the forceps cups 30 through the guide tube 30, so that the forceps cups contact the diseased part at the inner wall of the body cavity. Thereafter, the slider body 71 is moved backwardly relative to the holder 60 by the operator. Then, the wire 20 is retracted under the effect of the coil spring 85 through the receiving member 80, and the tensile force of the wire 20 is transmitted to the link mechanism 40 to thereby close the pair of forceps cups 30. As a consequence, a piece of meat of the diseased part is gathered into the forceps cups 30. At that time, the force for closing the pair of forceps cups 30 depends solely on the coil spring 85 and does not depend on the operator's force for moving the slider body 71 backwardly at all. The reason is that the slider 70 and the wire 20 are not connected together. Accordingly, since no large force is applied to the wire 20, it can be prevented such inconveniences that the wire 20 is accidentally cut off.

When the pair of forceps cups 30 is closed as mentioned, the retracting action of the wire 70 is finished and the receiving member 80 is returned to its original position. Accordingly, any attempt to further retreat the slider body 71 causes the push member 73 of the slider 70 to separate from the receiving member 80. In order to close the pair of forceps cups 30, it is just enough to move the slider body 71 backwardly simply by releasing the force of the finger applied to the slider body 71 rather than moving the slider body 71 backwardly by the operator's force, because when the force of the finger is released, the slider body 71 is moved backwardly under the effect of the coil spring 85.

By seeing the gradations 100 indicating the location of the fixing thread 90, it can be confirmed whether or not the receiving member 80 returns to its original position, namely, whether or not the pair of forceps cups 30 is closed. When it should occur that the forceps cups 30 is not closed under the effect of the coil spring 85, the fixing thread 90 may be moved backwardly directly by the hand. By doing this, the wire 20 is tensioned and the forceps cups 30 is closed.

When it is desired to change the force for closing the pair of forceps cups 30, the fixing thread 90 is temporarily released and the axial position of the receiving member 80 is adjusted. At such an adjusted position, the fixing thread 90 is tightened again to fix the receiving member 80 to the terminal tube 25. As a consequence, since the compressed state of the coil spring 85 can be changed, the tensile force of the wire 20 can be changed. At that time, the strength of the coil spring 85 can be confirmed through the gradations 100.

The present invention is not limited to the above embodiment but many modifications can be made. The receiving means may be constituted of first and second receiving members which are separated in the axial direction of the wire. In that case, the first receiving member receives the force (force for retracting the wire) of the coil spring, and the second receiving member receives the force (force for moving the wire forwardly) from the slider.

The forceps instrument of the present invention may be applied to a hard endoscope. At that time, the guide tube of the forceps instrument may have hard properties.

What is claimed is:

1. A forceps instrument for an endoscope comprising:
   (a) a guide tube capable of piercing all the way through a channel of said endoscope;
   (b) a wire extending through said guide tube;
   (c) a pair of forceps cups openably and closably provided on a distal end of said guide tube;
   (d) a link mechanism for connecting a distal end of said wire with said pair of forceps cups, said link mechanism opening said pair of forceps cups in response to a forward movement of said wire and closing said pair of forceps cups in response to a backward movement of said wire; and
   (e) a control mechanism disposed on a rear end of said guide tube and for remote controlling said pair of forceps cups through said wire, said control mechanism comprising:
   (i) a holder, said holder including a rod portion connected to the rear end of said guide tube, said rod portion having a receiving space;
   (ii) a slider axially slidably disposed on said rod portion of said holder, said slider being disconnected from said wire;
   (iii) receiving means mounted on a rear end portion of said wire in said receiving space of said holder, said receiving means being disposed forwardly of said slider and pushed by said slider when said slider slides forwardly; and
   (iv) a spring for biasing said receiving means backwardly.

2. A forceps instrument for an endoscope according to claim 1, in which said spring consists of a compressed coil spring, said coil spring being disposed between a surface for defining a distal end of said receiving space of said rod portion and said receiving means, said coil spring surrounding the rear end portion of said wire, said receiving space of said holder comprising an axially extending slit which is opened at a peripheral surface of said rod portion.

3. A forceps instrument for an endoscope according to claim 2, in which said receiving means includes a protrusion protruding outwardly from said slit of said rod portion.

4. A forceps instrument for an endoscope according to claim 2, in which said slider includes a slider body disposed on an outer periphery of said rod portion of said holder, and a push member disposed in said slit and connected to said slider body, said receiving means being pushed by said push member when said slider body slides forwardly.

5. A forceps instrument for an endoscope according to claim 4, in which said receiving means comprises a receiving member, said receiving member receiving a forward-directing force from said push member and a backward-directing force from said spring.

6. A forceps instrument for an endoscope according to claim 5, in which said receiving member is formed therein with a through-hole, the rear end portion of said wire being pierced into said through-hole thereby enabling to adjust an axial position of said receiving member relative to the rear end portion of said wire, said receiving member being releasably fixed by fixing means at an adjusted position, a distal end face of said push member being formed therein with a receiving hole for receiving the rear end portion of said wire.

7. A forceps instrument for an endoscope according to claim 6, in which said fixing means comprises a fixing thread, said fixing thread including a threaded portion and a handle portion, an inner end of said threaded portion, when radially threaded into said receiving member, pushing an outer peripheral surface of the rear end portion of said wire, an outer end of said threaded portion being located outside of said rod portion, said handle portion being fixed to the outer end of said threaded portion.

8. A forceps instrument for an endoscope according to claim 7, in which said rod portion of said holder is provided on the peripheral surface thereof with gradations for confirming the location of said threaded portion of said fixing thread.

* * * * *